(12) United States Patent
Xu et al.

(10) Patent No.: US 8,748,130 B2
(45) Date of Patent: Jun. 10, 2014

(54) HUMAN PAPILLOMAVIRUS / II-KEY HYBRIDS AND METHODS OF USE

(75) Inventors: Minzhen Xu, Northborough, MA (US); Eric von Hofe, Wellesley, MA (US)

(73) Assignee: Antigen Express, Inc., Worcester, MA (US)

( * ) Notice: Subject to any disclaimer, the term of this patent is extended or adjusted under 35 U.S.C. 154(b) by 822 days.

(21) Appl. No.: 12/552,064

(22) Filed: Sep. 1, 2009

(65) Prior Publication Data

US 2010/0080817 A1    Apr. 1, 2010

Related U.S. Application Data

(60) Provisional application No. 61/169,908, filed on Apr. 16, 2009, provisional application No. 61/093,606, filed on Sep. 2, 2008.

(51) Int. Cl.
  *C12N 15/00* (2006.01)
  *A61K 39/00* (2006.01)

(52) U.S. Cl.
  USPC ...................................... 435/69.7; 424/230.1

(58) Field of Classification Search
  None
  See application file for complete search history.

(56) References Cited

U.S. PATENT DOCUMENTS

| | | | |
|---|---|---|---|
| 5,559,028 A | 9/1996 | Humphreys | |
| 5,856,456 A | 1/1999 | Whitlow et al. | |
| 5,910,300 A | 6/1999 | Tournier et al. | |
| 5,919,639 A | 7/1999 | Humphreys et al. | |
| 6,210,903 B1 * | 4/2001 | De Leys | 435/7.1 |
| 6,432,409 B1 * | 8/2002 | Humphreys et al. | 424/192.1 |
| 7,026,443 B1 * | 4/2006 | Sette et al. | 530/300 |
| 7,179,645 B2 * | 2/2007 | Humphreys et al. | 435/320.1 |
| 7,205,274 B2 * | 4/2007 | Humphreys et al. | 514/20.6 |
| 7,541,334 B2 * | 6/2009 | Humphreys et al. | 514/1.1 |
| 2004/0058881 A1 | 3/2004 | Humphreys et al. | |
| 2006/0247190 A1 * | 11/2006 | Beach et al. | 514/44 |
| 2008/0095798 A1 | 4/2008 | Humphreys et al. | |
| 2010/0196353 A1 * | 8/2010 | Van Der Burg et al. | 424/130.1 |

OTHER PUBLICATIONS

Xu, M., Arneimittelforschung. 1999, 49:791-9.
Adams, S., Arneimittelforschung. 1997 47:1069-1077.
Humphreys, R.E., Vaccine. 2000 18:2693-2697.
Adams, S., Eur J. Immunol. 1995 25:1693-1702.
NCBI submission AAD33253.1 Jun. 2000, [Retrieved from the internet Dec. 9, 2009: <URL: http://www.ncbi.nlm.nih.gov/protein/4927721>]; sequence listing.
Van der Buro et al. Natural T-helper immunity against human papillomavirus type 16 (HPV16) E7-derived peptide epitopes in patients with HPV16-positive cervical lesions; identification of 3 human leukocyte antigen class II-restricted epitopes. International Journal of Cancer 2001, 91:612-618; Abstract, p. 612, para 1; p. 613, para 2, 10; p. 614, para 2; p. 615, para 2.
Xu, et al., "Ii-Key/HPV16 E7 hybrid peptide immunotherapy for HPV16+ cancers", Vaccine, vol. 27, No. 34, Jul. 2009, pp. 4641-4647.
Kallinteris, et al., "Enhanced CD4+ T-Cell Response in DR4-Transgenic Mice to a Hybrid Peptide Linking the Ii-Key Segment of the Invariant Chain to the Melanoma gp100(48-58) MHC Class II Epitope" Journal of Immunotherapy, vol. 28, No. 4, Jul. 2005, pp. 352-358.

\* cited by examiner

*Primary Examiner* — Agnieszka Boesen
(74) *Attorney, Agent, or Firm* — Pierce Atwood LLP; Kevin M. Farrell; David J. Wilson

(57) ABSTRACT

The present invention is directed towards compositions comprising Ii-Key/HPV hybrid peptides. The hybrid peptides of the present invention are effective in the generation of CD4+ helper T cell immune responses directed towards the specific HPV epitopes encoded in the hybrid peptide. The inclusion of the Ii-key peptide in the hybrid causes the peptide to have greater immunogenicity as compared to control peptide. The inclusion of Ii-Key/HPV hybrid in a peptide vaccine formulation composing both HPV hybrid and HPV CTL epitope peptide (administered concurrently or sequentially) leads to a greater CTL activity against HPV CTL epitopes. The hybrid peptides of the present invention may be useful, for example, for the immunization of subjects against HPV.

4 Claims, 4 Drawing Sheets

SEQUENCE LISTING

```
<160> NUMBER OF SEQ ID NOS: 20

<210> SEQ ID NO 1
<211> LENGTH: 30
<212> TYPE: PRT
<213> ORGANISM: Human papillomavirus type 16

<400> SEQUENCE: 1

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp
            20                  25                  30

<210> SEQ ID NO 2
<211> LENGTH: 19
<212> TYPE: PRT
<213> ORGANISM: Human papillomavirus type 16

<400> SEQUENCE: 2

Leu His Glu Tyr Met Leu Asp Leu Gln Pro Glu Thr Thr Asp Leu Tyr
1               5                   10                  15

Cys Tyr Glu

<210> SEQ ID NO 3
<211> LENGTH: 15
<212> TYPE: PRT
<213> ORGANISM: Human papillomavirus type 16

<400> SEQUENCE: 3

Leu His Glu Tyr Met Leu Asp Leu Gln Pro Glu Thr Thr Asp Leu
1               5                   10                  15

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
                          peptide
<220> FEATURE:
<221> NAME/KEY: MOD_RES
<222> LOCATION: (5)..(5)
<223> OTHER INFORMATION: 5-aminovaleric acid

<400> SEQUENCE: 4

Leu Arg Met Lys Xaa Leu His Glu Tyr Met Leu Asp Leu Gln Pro Glu
1               5                  10                  15

Thr Thr Asp Leu
            20

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 5-aminovaleric acid

<400> SEQUENCE: 5

Leu Arg Met Lys Xaa His Glu Tyr Met Leu Asp Leu Gln Pro Glu Thr
1               5                  10                  15

Thr Asp Leu

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 5-aminovaleric acid

<400> SEQUENCE: 6

Leu Arg Met Lys Xaa Glu Tyr Met Leu Asp Leu Gln Pro Glu Thr Thr
1               5                  10                  15

Asp Leu

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 5-aminovaleric acid

<400> SEQUENCE: 7

Leu Arg Met Lys Xaa Tyr Met Leu Asp Leu Gln Pro Glu Thr Thr Asp
1               5                  10                  15

Leu

<210> SEQ ID NO 8
<211> LENGTH: 10
<212> TYPE: PRT
<213> ORGANISM: Human papillomavirus type 16
```

```
<400> SEQUENCE: 8

Tyr Met Leu Asp Leu Gln Pro Glu Thr Thr
1               5                   10

<210> SEQ ID NO 9
<211> LENGTH: 16
<212> TYPE: PRT
<213> ORGANISM: Unknown
<220> FEATURE:
<223> OTHER INFORMATION: Description of Unknown: Mammalian li-key
      peptide

<400> SEQUENCE: 9

Leu Arg Met Lys Leu Pro Lys Pro Pro Lys Pro Val Ser Lys Met Arg
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Arg Met Lys Leu Pro Lys Pro Pro Lys Pro Val Ser Lys Met Arg
1               5                   10                  15

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Arg Met Lys
1

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu His Glu Tyr Met Leu Asp Leu Gln Pro Glu Thr Thr Asp Leu Gly
1               5                   10                  15

Gly Tyr Pro Tyr Asp Val Pro Asp Tyr Ala
            20                  25

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 5-aminovaleric acid

<400> SEQUENCE: 13

Leu Arg Met Lys Xaa Glu Tyr Met Leu Asp Leu Gln Pro Glu Thr Thr
```

-continued

```
                 1               5              10              15

Asp Leu Gly Gly Tyr Pro Tyr Asp Val Pro Asp Tyr Ala
                20              25

<210> SEQ ID NO 14
<211> LENGTH: 9
<212> TYPE: PRT
<213> ORGANISM: Human papillomavirus type 16

<400> SEQUENCE: 14

Arg Ala His Tyr Asn Ile Val Thr Phe
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Pro Tyr Asp Val Pro Asp Tyr Ala
1               5

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Arg Met Lys
1

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Arg Met Lys Leu Pro Lys
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Arg Met Lys Leu Pro Lys Ser
1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 19

Leu Arg Met Lys Leu Pro Lys Ser Ala Lys Pro
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Arg Met Lys Leu Pro Lys Ser Ala Lys Pro Val Ser Lys
1               5                   10
```

US 8,748,130 B2

HUMAN PAPILLOMAVIRUS / Ii-KEY HYBRIDS AND METHODS OF USE

BACKGROUND OF INVENTION

Every year, 470,000 cases of cervical cancer are diagnosed. Essentially 100% of cervical cancers contain HPV of the high-risk type (HPV 16 or 18), persistent infection of the cervix with these viruses is considered to be the necessary cause of the disease (90% of other ano-genital cancers also contain HPV). Oral cancer, penile cancer and some neck cancer might be related to HPV infection as well. There are no good therapies when metastasis of HPV induced cancers such as cervical cancer occurs and thus effective new therapies are needed urgently.

Prophylactic vaccines for HPV infection are already approved by the FDA. Gardasil, a virus like particle that targets the L1 protein of HPV types 6, 11, 16 and 18 protects women from infection by HPV close to 100%. This type of vaccine mainly induces a humeral immune response generating antibodies that can neutralize the virus. Gardasil is thus an effective vaccine for preventing HPV infection. However, this kind of vaccine is ineffective for treating HPV+ cancers since both CD4+ and CD8+ T cell immunity must be induced in order to eradicate the HPV+ cancers.

Accumulating data indicate that immunotherapy for cervical cancer and other HPV+ cancers holds promise. The expression of the HPV E6 and E7 genes is found in most cervical cancers as well as other HPV+ cancers, indicating that the HPV oncogenic proteins, E6 and E7, are critical for the induction and maintenance of cellular transformation. The specific expression of these genes in the majority of the HPV+ carcinomas suggests that they are good targets for immunotherapy.

There are several types of therapeutic vaccines being studied currently. 1) Viral vector-based DNA vaccine such as recombinant adenovirus that contains E6 and/or E7 genes. The advantage of this vaccine is that it is a strong immunogen. Disadvantages include safety and cost. 2) Plasmid-based DNA vaccine. The advantage is that these are generally considered safe and economical to produce but so far have proven to be only weakly immunogenic with a low in vivo transfection rate. 3) Peptide vaccine. The advantages are that it is very safe and economical but peptides are generally only weakly immunogenic and HLA-restricted. 4) Protein vaccination. The big advantage here is safety: however, they do not induce good cellular immunity. 5) Dendritic cell (DC)-based vaccine. Autologous DCs pulsed with E7 or E6 proteins are very immunogenic. The disadvantage is the high cost and the labor-intensive methods required for each vaccination.

Thus, an efficient yet safe immunotherapy is needed for treating or preventing HPV+ tumors.

SUMMARY OF INVENTION

Presented herein, are embodiments of the present invention including a novel and non-obvious method that significantly enhances the efficiency of HPV peptide vaccine. In this regard, the present invention is directed towards compositions comprising Ii-key/HPV hybrid peptides and nucleotide sequences encoding said peptides. The present invention is also directed towards methods of prevention of HPV infection by administration of one or more compounds of the present invention to a subject. Further, the present invention is directed towards the treatment of diseases in which HPV infection is at least part of the etiology of the disease. Such diseases include, but are not limited to, warts and precancerous or cancerous lesions such as cervical cancer, penile cancer and certain neck cancers. In another aspect of the present invention, it is contemplated that the HPV sequences of the present invention are useful for the inoculation and vaccination of subjects for the treatment or prevention of diseases in which HPV infection is at least part of the etiology of the disease.

In another aspect, the present invention relates to a method to improve the potency of DNA and peptide vaccines containing MHC Class II-presented epitopes of HPV antigens of interest. The present invention involves priming the immune system of a subject with Ii-Key hybrid peptides such that the potency of a subsequently administered DNA or peptide vaccine is augmented. The Ii-Key construct may be administered in the form of a nucleic acid construct encoding the Ii-Key hybrid peptide.

A non-limiting example is the use of Ii-Key antigenic epitope hybrids in vaccination protocols to protect against HPV. By first priming naive T-helper cells with a hybrid protein comprised of Ii-Key and a highly conserved MHC class II epitope derived from the HPV protein, the immunological response to a clinically tested or probable HPV vaccine used in the prevention and treatment of HPV infection is improved. By priming a subject's immune system with these hybrid peptides before boosting with a DNA or protein vaccine, limited supplies of vaccines can be extended or doses reduced effecting greater safety.

In another aspect, this invention relates to compositions used to increase the potency of DNA and peptide vaccines by priming the subject's immune response. The compositions are hybrid peptides comprised of the LRMK (SEQ ID NO: 11) amino acid residues of the Ii-Key protein and an MHC class II epitope, wherein the epitope is a known or suspected HPV epitope.

DETAILED DESCRIPTION OF INVENTION

Figure 1:
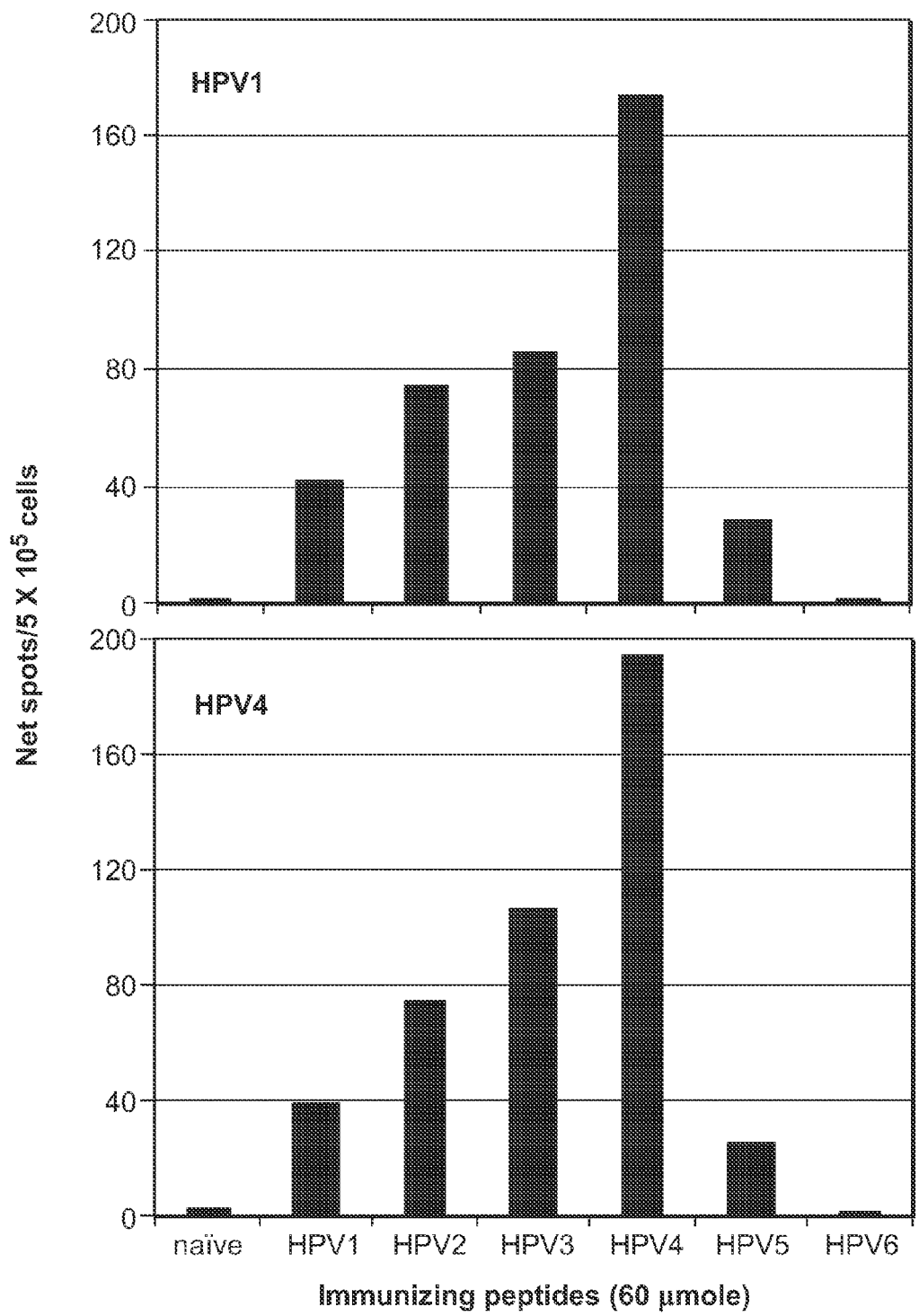
FIG. 1 shows data demonstrating the most active HPV hybrids in HLA-DR4-tg (transgenic) mice. HLA-DR4-tg mice (3 mice/group) were immunized with 60 nmole of the indicated peptide in an equal volume of CFA (100 μl/mouse total volume). Three weeks after immunization, pooled splenocytes were obtained for IFN-γ ELISPOT following in vitro stimulation with the epitope-only peptide HPV1 or Ii-Key hybrids (HPV1-6, only the results of HPV1 (top) and HPV4 (bottom) are shown). The frequency of IFN-γ secreting cells in splenocytes from HPV4 immunized mice was approximately 5-fold greater than the frequency in splenocytes from HPV1 immunized mice. Comparable results were obtained from a repeat study.

The hybrid compositions and methods of use disclosed herein have been designed to overcome the shortcomings of conventional peptide vaccines and immunostimulatory agents. The hybrid vaccines of the present invention comprise an HPV epitope, the Ii-key peptide (or portion or modification thereof) and a spacer, herein referred to as an Ii-Key/MHC class II hybrid construct or hybrid peptide. By taking advantage of the Ii-Key protein interaction with MHC class II molecules, the compositions and methods of the present invention enhance the binding of antigenic epitope of HPV to the MHC class II molecule binding groove, bypassing the normal antigen processing pathway. In this context, antigen can then be presented to the immune system, stimulating a specific CD4+ T lymphocyte response. Due to the increased potency of Ii-Key/MHC class II hybrids in stimulating immune response, less efficiency in the process can be tolerated and it may not require the use of immune system stimulants.

Thus, described herein are compositions and methods of treating a HPV infection and associate diseases and/or cancers in humans, the disease or cancer being characterized by the presence of HPV. Described herein are compositions and methods for the prevention of HPV infection. As noted in the Background section, cancers which are thought or known to have HPV infection as at least part of their etiology include cervical cancer, penile cancer and others. Other diseases associated with HPV infection include, for example, warts. The methods of the present invention comprise providing an Ii-Key/MHC class II hybrid construct in a pharmaceutically acceptable carrier and vaccinating a patient with the hybrid, under conditions appropriate for the stimulation of an immune response. The hybrid construct may be administered as an Ii-Key hybrid peptide or in the form of a nucleic acid encoding an Ii-Key hybrid peptide.

The Ii-Key/MHC class II hybrid peptide comprises the LRMK (SEQ ID NO: 11) (and a modified form: YRMK (SEQ ID NO: 16)) amino acid residues of the Ii protein linked directly or indirectly to the N-terminus of an MHC class II epitope containing segment of an HPV. In this regard, the Ii-key residues and the HPV epitope should be, but need not be, separated by a distance falling within a range corresponding to the length of about two to twenty amino acid residues. This space can contain a variety of linkers (or spacers), including a simple polymethylene (ava) linker, the natural sequence of Ii extending from the C-terminus of LRMK, (SEQ ID NO: 11), or the natural sequence of HPV extending from the N-terminus of the HPV epitope. Examples of additional suitable linkers, as well as various alternate embodiments of Ii-key hybrid peptides, are given in U.S. Pat. No. 7,179,645 issued Feb. 20, 2007, and U.S. Pat. No. 7,205,274, issued Apr. 17, 2007, which are incorporated herein by reference. The method results in the stimulation of a CD4+ T cell response. Similarly, the hybrid construct can be administered in the form of a nucleic acid encoding an Ii-Key/HPV hybrid peptide. To provide specificity to the options outlined in the preceding text, it is necessary to discuss the anatomy of the hybrid Ii-key peptide of the present invention in greater detail.

The Linker

The linker (or spacer) is an intervening chemical structure covalently linking the N-terminal and C-terminal elements of the hybrid, the chemical structure being a covalently joined group of atoms which when arranged in a linear fashion forms a flexible chain which extends up to the length of 20 amino acids likewise arranged in a linear fashion. Thus, to the extent that the linker sequence is comprised of amino acids (which is not a requirement), the disclosure of the present invention provides an additional functionality to the amino acid residues of the linker, above and beyond their required role as space occupiers.

The specified linker length (up to the length of 20 amino acids arranged in a linear fashion) may be long enough to contain a second complete epitope whether it be a complete MHC Class II epitope, a complete MHC Class I epitope, or a complete ARD (antibody-recognized determinant) or segments of such additional epitopes. Additionally, such a sequence length can accommodate a plurality of non-overlapping epitopes selected from the group consisting of MHC Class I epitopes, MHC Class II epitopes and ARDs.

Where the intervening chemical structure comprises one or more epitopes/determinants, the overall length within defined limits is dictated to a large extent by the identity and of the epitope/determinant. In the case in which the intervening chemical structure is antigenically neutral, the teachings of U.S. application Ser. No. 09/396,813, now U.S. Pat. No. 6,432,409 (incorporated herein by reference in its entirety), apply. As indicated for antigenically neutral spacers, for example, the spacer is preferably less than the length of a peptidyl backbone of 9 amino acids linearly arranged. Optimally, spacer length is the length of a peptidyl backbone of between 4 and 6 amino acids, linearly arranged. Preferably, the spacer is unable to hydrogen bond in any spatially distinct manner to other distinct elements of the enhancing hybrid peptide.

With further respect to antigenically neutral spacer elements, various chemical groups may be incorporated in the spacer segment instead of amino acids. Examples are described in U.S. Pat. No. 5,910,300, the contents of which are incorporated herein by reference. In a preferred embodiment the spacer is comprised of an aliphatic chain optimally interrupted by heteroatoms, for example a $C_2$ $C_6$ alkylene, or $=N-(CH_2)_2-6-N=$. Alternatively, a spacer may be composed of alternating units, for example of hydrophobic, lipophilic, aliphatic and aryl-aliphatic sequences, optionally interrupted by heteroatoms such as O, N, or S. Such components of a spacer are preferably chosen from the following classes of compounds: sterols, alkyl alcohols, polyglycerides with varying alkyl functions, alkyl-phenols, alkyl-amines, amides, hydroxyphobic polyoxyalkylenes, and the like. Other examples are hydrophobic polyanhydrides, polyorthoesters, polyphosphazenes, polyhydroxy acids, polycaprolactones, polylactic, polyglycolic polyhydroxy-butyric acids. A spacer may also contain repeating short aliphatic chains, such as polypropylene, isopropylene, butylene, isobutylene, pentamethlyene, and the like separated by oxygen atoms. Linkers may also be, for example, repeating methane groups ($—CH_3—$).

Additionally, peptidyl sequences which can be used in a spacer are described in U.S. Pat. No. 5,856,456, the contents of which are incorporated herein by reference. In one embodiment, the spacer has a chemical group incorporated within which is subject to cleavage. Without limitation, such a chemical group may be designed for cleavage catalyzed by a protease, by a chemical group or by a catalytic monoclonal antibody. In the case of a protease-sensitive chemical group, tryptic targets (two amino acids with cationic side chains), chymotryptic targets (with a hydrophobic side chain) and cathepsin sensitivity (B, D or S) are favored. The term "tryptic target" is used herein to describe sequences of amino acids which are recognized by trypsin and trypsin-like enzymes. The term "chymotryptic target" is used herein to describe sequences of amino acids which are recognized by chymotrypsin and chymotrypsin-like enzymes. In addition, chemical targets of catalytic monoclonal antibodies and other chemically cleaved groups are well known to persons skilled in the art of peptide synthesis, enzymic catalysis and organic chemistry in general, and can be designed into the hybrid structure and synthesized using routine experimental methods.

Not all embodiments of the present invention include immunogenic neutrality of the intervening chemical structure or spacer. That is, the present invention includes embodiments in which the intervening chemical structure, or spacer, is selected from the group consisting of: 1) an MHC Class I epitope, or a portion thereof; and 2) an antibody-recognized determinant, or a portion thereof.

The Ii-key hybrids of the present invention may include spacers that vary from totally peptide in character to containing portions that are substantially non-peptide in character. In view that some homologs are substantially reduced or nonpeptide in character, they will be more likely to have favorable properties such as, for example, penetration through cellular membranes, solubility, resistance to proteolysis, resistance to inactivation by conjugation, oral bioavailability and longer half life in vivo.

Preferred spacers include one or more simple polymethylene (ava) linkers.

Minimum sequences (or lengths) are preferred for several reasons. These include simplicity and cost of synthesis, less opportunity for proteolytic degradation, less opportunity for metabolic change leading to clearance or adsorption. Thus, the linker element may contain a plurality of epitopes which overlap one another (i.e., an individual amino acid residues may be a components of more than one epitope). Similarly, the C-terminal element which includes an HPV peptide of the present invention may also contain additional epitopes (MHC Class I, MHC Class II or ARD) in an overlapping or non-overlapping arrangement.

It is noted that the boundaries between the various elements of the Ii-key hybrid peptide of the present invention are, within certain stated limits, somewhat arbitrary. Epitopes spanning the junctions between the various elements are encompassed within the scope of the present invention. Thus, for example, where a claim specifies that a portion of an epitope is contained within one of the enhancing hybrid peptide elements or domains (e.g., the linker region), this necessarily implies that the remaining portion is found in a contiguous portion of a flanking portion or domain. Partial (i.e., non-functional epitopes) are of no utility in connection with the present invention except as, perhaps, space fillers.

It is also known in the art that functional MHC Class I epitopes, MHC Class II epitopes and ARDs may be arranged in an overlapping manner while retaining full functionality of all represented epitopes. The respective functions of each epitope within a hybrid are not co-expressed at one point in time on a per peptide basis because such peptides must be bound into MHC Class I or MHC Class II molecules and recognized in a folded structure by an antibody. Nevertheless, given a population of administered (e.g., injected) peptides with respective processing and/or binding to cell surface MHC molecules, all three classes of epitopes within any one Ii-Key enhancing hybrid can be effective immunogens within an immunized animal.

The Ii-Key Peptide

Early work in this area demonstrated that the mammalian Ii key peptide LRMKLPKPPKPVSKMR [SEQ ID NO.: 9], and a modified mammalian Ii-key peptide, YRMKLPKPPKPVSKMR [SEQ ID NO.: 10], have the ability to alter presentation of certain MHC Class II-restricted, antigenic peptides to T lymphocyte-hybridomas which recognize those respective antigenic peptides (U.S. Pat. No. 5,559,028; U.S. Pat. No. 5,919,639, the disclosures of which are incorporated herein by reference). Previous experiments with modified versions of the Ii-key peptide have indicated that a wide variety of modifications can be made to this polypeptide without detriment to activity. Indeed, modifications often enhanced antigen presentation activity of the polypeptide.

Results detailed in the Exemplification section of U.S. application Ser. No. 09/396,813, now U.S. Pat. No. 6,432,409 (which is herein incorporated by reference in its entirety), indicate that all modified Ii-key peptides which retain antigen presentation enhancing activity will function in the enhancing hybrid of the present invention when appropriately incorporated. Modifications of the Ii-key peptide include deletion of one or more amino acids from the C-terminus, protection of the N-terminus, amino acid substitutions and introduction of cyclical peptides. Deletions of the Ii-key peptide which retain at least 4 contiguous amino acids of the original sequence (LRMK (SEQ ID NO: 11)), or a substituted version thereof (YRMK, (SEQ ID NO: 16)) exhibit functional activity. Various natural or non-natural amino acids may be substituted at respective residue positions. Some examples of molecules which may be substituted are peptidomimetic structures, D-isomer amino acids, N-methyl amino acids, L-isomer amino acids, modified L-isomer amino acids, and cyclized derivatives. In addition, procedures of medicinal chemistry may be applied by one skilled in the art using routine experimental methods to obtain additional modifications of the N-terminal segment of hybrids. Examples of such procedures are methods of rational drug design, molecular modeling based on structural information from X-ray diffraction data, nuclear magnetic resonance data (and other computational methods), screening of products of combinatorial chemical syntheses and isolations of natural products. Examples of modified versions of Ii-key peptide which are known to retain high activity are LRMK [SEQ ID NO: 11], LRMKLPK [SEQ ID NO: 17], LRMKLPKS [SEQ ID NO:

18], LRMKLPKSAKP [SEQ ID NO: 19], and LRMKLPK-SAKPVSK [SEQ ID NO: 20]. Other modifications and modified versions of the Ii-key peptide are described in U.S. Pat. No. 5,919,639 and U.S. Pat. No. 5,559,028 (both of which are incorporated herein by reference in their entirety). A modified version of the Ii-key peptide (YRMKLPKPPKPVSKMR, [SEQ ID NO: 10]) which is known to retain activity is referred to herein as an "Ii-key homolog." The term Ii-key homolog as used herein is inclusive of the Ii-key peptide itself.

Such Ii-Key peptides were demonstrated by several experimental methods to bind to an allosteric site at the end of the antigenic peptide binding site of MHC Class II molecules (Xu, M., Arneimittelforschung. 1999 49:791 9). That process of binding to the allosteric site facilitated the release and exchange of endogenously bound antigenic peptide with cell surface MHC Class II molecules.

Peptide homologs of the Ii-Key peptide act on murine or human MHC Class II molecules to promote the release of bound antigenic peptides and their replacement with synthetic peptides (Adams, S., Arneimittelforschung. 1997 47:1069 1077; Xu, M., Arneimittelforschung. 1999 49:791 9). Hybrid constructs of the Ii-Key peptide linked to an antigenic epitope peptide through either a simple polymethylene linker or the extended, natural sequence of the Ii protein, have 500 to 2000 times the potency of presentation versus the antigenic peptides (Humphreys, R. E., Vaccine. 2000 18:2693 2697). This property has great clinical utility in diagnosis, treatment monitoring and therapy of various diseases and conditions, as presented herein. This activity of the Ii-Key moiety within Ii-Key/antigenic epitope hybrids is found either in vitro or in vivo. This activity can be ascribed to interaction with cell surface MHC Class II molecules because the Ii-Key compounds were active in vitro with either living or paraformaldehyde-fixed antigen presenting cells (Adams, S., Eur J. Immunol. 1995 25:1693 1702). However, since the compounds are potent in vivo, they may also be taken up by the pathway which processes exogenous antigens and bind to MHC Class II molecules in the post-Golgi, antigen charging compartment.

The HPV Epitopes

Although the present invention is not limited to any particular HPV epitope or epitope-containing peptide exemplary non-limiting examples of the HPV epitopes (useful, for example, alone or in epitope-containing peptides) of the present invention include MHC class II epitopes HPV16 E7 (8-26) [SEQ ID NO:2], HPV16 E7 (8-22) [SEQ ID NO:3], HPV16 E7 (9-22) [SEQ ID NO.: 5], HPV16 E7 (10-22) [SEQ ID NO.: 6], HPV16 E7 (11-22) [SEQ ID NO.: 7] or HPV16 E7 (10-20) [SEQ ID NO.: 8] which are contained within the peptide mhgdtptlheymldlqpettdlycyeqlnd [SEQ ID NO.: 1]. The present invention is not limited to HPV16 E7 hybrids. In another aspect of the invention, other HPV16 epitopes are contemplated and HPV18 epitopes are also contemplated including MHC Class I and MHC Class II epitopes. In yet another aspect of the invention one or both of the HVP16 and HPV 18 epitopes can be used in a vaccine and/or in the Ii-key hybrid of the present invention and can be administered either simultaneously or sequentially.

The methods of the present invention include treating a patient by vaccination with an Ii-Key/HPV hybrid construct whereby the stimulation of a CD4+ T cell response specific to the specific HPV epitope is initiated or enhanced. As shown in the Exemplification section, ELISPOT assays show increased CD4+ T cell response to the HPV peptide as compared to native HPV peptide. Additionally, vaccines may also include MHC Class I epitopes with or without MHC Class II epitopes.

In one embodiment, the present invention includes treating a patient by vaccination with or administration of a compound of the present invention including an MHC class II epitope HPV16 E7 (8-26) [SEQ ID NO:2] or HPV16 E7 (8-22) [SEQ ID NO:3] or other epitopes, which are contained within the peptide mhgdtptlheymldlqpettdlycyeqlnd [SEQ ID NO.: 1] or by vaccination with a DNA or RNA encoding the same amino acid sequences, wherein the compound is not a Ii-key hybrid. In this regard, the DNA or RNA encoding the amino acid sequence would be operably linked to the necessary promoters, initiators, etc., known to those skilled in the art for the efficient transcription and/or translation of DNA and RNA, respectively. See, for example, Sambrook, et al., at www.MolecularCloning.com. Likewise, the Ii-key/HPV hybrids of the present invention may be administered as DNA or RNA encoding the hybrid of the present invention wherein the sequence would be operably linked to the necessary promoters, initiators, etc.

Ii-Key/HPV Hybrids and Uses Thereof

The methods of the present invention include treating a patient by vaccination with or administration of a compound of the present invention including an Ii-Key/MHC class II hybrid construct wherein the MHC class II epitope is HPV16 E7 (8-26) [SEQ ID NO:2] and/or HPV16 E7 (8-22) [SEQ ID NO:3].

In another embodiment, the present invention provides a pharmaceutical composition for use in the treatment or prevention of HPV infection and/or diseases caused by or augmented by HPV infection, the composition comprising an MHC class II epitope [SEQ ID NO:2 and/or SEQ ID NO:3], or an Ii-Key/MHC Class II hybrid construct in a pharmaceutically acceptable carrier. The Ii-Key/MHC Class II hybrid construct comprises the LRMK (SEQ ID NO: 11) residues of the Ii protein linked to the N-terminus of an MHC Class II epitope SEQ ID NO: 2 or 3. The LRMK (SEQ ID NO: 11) residues and the MHC class II epitope should be separated by a distance equivalent to the length of about two to twenty amino acid residues. This space can contain a variety of linkers, including a simple polymethylene (ava) linker, the natural sequence of Ii extending from the C-terminus of LRMK (SEQ ID NO: 11), or the natural sequence of HPV extending from the N-terminus of the MHC class II epitope. The Ii-Key/MHC Class II hybrid construct can also comprise a DNA encoding the same hybrid peptide. More specifically the present invention includes a composition wherein the MHC Class II epitope of the hybrid construct is contained within the peptide mhgdtptlheymldlqpettdlycyeqlnd [SEQ ID NO.: 1]. The composition of the present invention includes the hybrid construct comprising amino acids having any of the sequences listed in Table 2, below, or a DNA encoding the same. The results of ELISPOT assays in the Exemplification section, below, show that murine subjects vaccinated with Ii-Key/HPV hybrid constructs exhibit an increased CD4+ T cell response compared to native HPV peptide.

Such epitopes/determinants selected for use in the generation of an enhancing hybrid of the present invention may be further modified for use. That is to say, polypeptides of natural or modified sequence, peptidomimetic structures and, also, chemical structures which are not natural or modified amino acids may be included in the epitope/determinant elements of the enhancing hybrids disclosed herein. In addition, various chemical modifications may be made to the antigenic epitope/determinant element of the enhancing hybrid. For example, the addition, in whole or in part, of non-natural amino acids or of other backbone or side chain moieties wherein the modifications preserve binding specificities of the antigenic epitope/determinant. Such chemical structures might bear moderate, little or no apparent structural resemblance to any antigenic peptide which is derived from a natural protein sequence. Such modifications might or might not bear on recognition by T cell receptors. Modifications may increase recognition of the antigenic epitope (e.g., lead to recognition by previously non-recognizing subsets of T cell receptors).

The present invention further provides a pharmaceutical composition for use in the treatment or prevention of HPV infection and/or diseases caused by or augmented by HPV infection, comprising an adjuvant and an MHC class II epitope or an Ii-Key/MHC Class II hybrid construct in a pharmaceutically acceptable carrier. The Ii-Key/MHC Class II hybrid construct comprises the LRMK (SEQ ID NO: 11) residues of Ii-Key protein linked to the N-terminus of an MHC Class II epitope containing segment of HPV. The construct can also comprise a DNA encoding the same hybrid peptide. The composition provided may include, but not limited, to the adjuvant GM-CSF.

CD4+ T helper cells play a critical role in the activation and maintenance of CD8+ cytotoxic T lymphocytes (CTL). Thus, activation of antigen-specific CD4+ T cells is critical for vaccine design. A potent HPV+ cancer therapeutic vaccine should be safe, economical to produce and efficient. Peptide vaccines are safe and economical to produce. One embodiment of the present invention is directed towards a novel and inventive technology to significantly enhance the efficiency of peptide vaccines. Linking the Ii-Key functional group LRMK (SEQ ID NO: 11) through a polymethylene linker to a MHC class II epitope significantly enhances the CD4+ T cell response to that epitope in both murine models and they have shown activity in clinical trials.

In the Exemplification section below, Ii-Key hybrid technology was used to create potent peptide immunotherapy for HPV+ cancers. A promiscuous HLA-DR restricted HPV16 E7 epitope was defined: HPV16 E7 (8-22). With HPV16 E7 (8-22), a homologous series of Ii-Key/HPV16 E7 (8-22) hybrids have been synthesized to test the influence of spacer length on the in vivo enhancement of HPV16 E7 (8-22)-specific CD4+ T lymphocyte responses. HLA-DR4 transgenic mice were immunized with Ii-Key/HPV16 E7 (8-22) hybrids along with the HPV16 E7 (8-22) and HPV16 E7 (11-20) epitope-only peptides (HLA-A2-restricted CTL epitopes) in CFA. As measured by IFN-γ ELISPOT assays, Ii-Key hybrids have exhibited more than 5-fold enhancement of CD4+ T cell activation in HLA-DR4 model systems compared to the HPV16 E7 (8-22) epitope-only peptide. Thus, these Ii-Key hybrids can generate a safe, simple, yet potent HPV peptide immunotherapy for HPV16+ tumors including cervical cancer and other cancers related to HPV infection.

Ii-Key/MHC class II hybrid vaccines can induce long-term, antigen-specific CD4+ T cell stimulation. The enhanced Th cell activation afforded by hybridization with Ii-Key represents an important advance in the design of peptide vaccines. Furthermore, the antigen-specific mechanism of T helper stimulation allows Ii-Key hybrid technology to be used together with other strategies (such as ISCOMATRIX™, CSL Behring, King of Prussia, Pa.) to further enhance the potency of the MHC class II vaccine peptides.

It will be recognized by one skilled in the art that the hybrid construct composition may be administered in the form of an Ii-Key hybrid peptide or as a nucleic acid construct encoding an amino-acid-based Ii-Key hybrid peptide. One skilled in the art, using routine experimental methods, could also substitute various natural or non-natural amino acids at respective residue positions in the hybrid peptide. Some examples of molecules which may be substituted are peptidomimetic structures, D-isomer amino acids, N-methyl amino acids, L-isomer amino acids, modified L-isomer amino acids, and cyclized derivatives.

Co-Stimulation

In one aspect, the present invention relates to a method for increasing the potency of a vaccine directed toward a pathogen of interest in a subject. A vaccine is provided in connection with this method. The vaccine can include, for example, traditional heat-killed or chemically inactivated virus. Alternatively, the vaccine can include isolated protein from the pathogen of interest, or fragments thereof. The vaccine can also include protein or peptides produced by recombinant DNA techniques, or synthetic peptides. The present invention includes methods of increasing vaccine potency wherein the pathogen of interest is a virus or a bacterium. More specifically, the present invention includes methods wherein the pathogen is an HPV virus including the HPV16 E7 strain of HPV. It is desirable to increase the potency of the vaccine so that the limited supply is effective for the immunization of as many individuals as possible and/or any negative effects of the actual vaccine are minimized.

The results disclosed herein demonstrate that the use of an Ii-key hybrid construct to prime the immune system of the subject prior to administration of the vaccine is surprisingly effective in increasing the potency of the vaccine relative to a non-primed administration. The Ii-key sequence has been described above. The Ii-key construct utilized in connection with the present invention includes at least the LRMK (SEQ ID NO: 11) residues of the Ii-key sequence joined, through a linker, to an MHC class II epitope which is found within the hybrid construct discussed above. The linker is sized to provide spacing between the Ii-key element and the MHC class II epitope which results in maximal enhancement of the immune response. Generally speaking, this spacer provides spacing between these elements that approximates the spacing that would be provided by an amino acid sequence of 15-25 amino acid residues. The linker need not be comprised of amino acids, although this composition does simplify production of the hybrid construct. Alternatives to the amino acid linker portion have been described in the prior art as noted above.

The immune system of the subject is primed using an Ii-key construct of the type described above. Generally speaking, the Ii-key hybrid construct is formulated for injection. This formulation includes a physiologically compatible buffer and, optionally, an adjuvant. Many adjuvants are known in the art and the selection of one adjuvant over another is a matter of routine experimentation. Typically, the administration of the Ii-key construction formulation is by intramuscular or subcutaneous injection.

Following a period of time sufficient for the immune system of the organism to respond to the Ii-key hybrid administration, the vaccine composition is administered. Like the Ii-key formulation, the vaccine composition is typically administered in a physiologically compatible buffer with or without an adjuvant. In another aspect an Ii-key hybrid is used as the vaccine after priming with the Ii-key hybrid. The Ii-key hybrid may or may not be the same hybrid used to prime the immune response. The results shown below demonstrate a remarkable enhancement in the potency of HPV vaccine compositions following priming with an Ii-key hybrid construct. Results are detailed in the Exemplification section. Further, the priming Ii-key hybrid and the vaccine composition may be co-administered (i.e., concurrent or co-stimulation).

It will be recognized by one skilled in the art that either the Ii-key hybrid construct or the vaccine composition may be administered in the form of a nucleic acid construct encoding an amino-acid-based vaccine or Ii-key construct. A DNA vaccine may be codon optimized to match the codon preferences of the subject. The literature is rich in the description of constructs and methods for the administration of DNA constructs for the purpose of stimulating an immune response with the encoded product. Many such constructs are virus-based, although mechanical methods of introduction (e.g., gene gun technology) can be employed.

The invention now being described, it will be apparent to one of ordinary skill in the art that many changes and modifications can be made thereto without departing from the spirit or scope of the invention.

EXEMPLIFICATION

Ii-Key/HPV16 E7 hybrid therapeutic vaccine
Methods:
Prediction of HLA-DR-Restricted Epitopes.

Computer algorithms (e.g., www.syfpeithi.de/scripts/MHCServer.dll/home.htm) have been used to analyze the possible HLA-DR-restricted epitopes in the HPV16 E7 sequence (AAD33253 from GenBank/PubMed). Using this algorithm method, it was determined that the peptide represented by amino acids 8 to 26 [SEQ ID NO.: 2] of the HPV16 E7 protein contains promiscuous HLA-DR epitopes.

TABLE 1

Sequence of first 30 amino acid and epitope of HPV16 E7.

| | |
|---|---|
| HPV16 E7 (1-30) | Mhgdtptlheymldlqpettdlycyeqlnd [SEQ ID NO.: 1] |
| HPV16 E7 (8-26) | Lheymldlqpettdlycye [SEQ ID NO.: 2] |
| HPV16 E7 (8-22) | Lheymldlqpettdl [SEQ ID NO.: 3] |

Design and Synthesis of Ii-Key/HPV16 E7 (8-22) Hybrids.

A homologous series of Ii-Key/HPV16 E7 (8-22) hybrids were synthesized to test the influence of spacer length on the in vivo enhancement of HPV16 E7 (8-22)-specific CD4+ T lymphocyte responses in HLA-DR4 transgenic mice. The Ii-key sequence is defined herein as LRMKLPKPPK-PVSKMR [SEQ ID NO.: 9]. The first four amino acids of the Ii-key sequence, the Ii-Key segment (LRMK [SEQ ID NO.: 11]), was linked by a flexible polymethylene spacer ava (5-aminovaleric acid=5-aminopentanoic acid) spacer to different amino acids at the N-terminus of the HPV16 E7 (8-22) epitope. The addition of other amino acids in the Ii-key sequence contiguous to the Ii-key segment was also contemplated herein for construction of the Ii-key/HPV hybrids of the present invention. All peptides were N-acetylated and C-amidated to inhibit exopeptidases. All peptides were synthesized by 21$^{st}$ Century Biochemicals (Marlboro, Mass.) with >95% purity. Since this epitope is mostly restricted by human HLA-DR4 allele, work first focused on testing HLA-DR4 activity because on the commercial availability of these transgenic mice. Tested first was the influence of spacer length whereby the ava linker was linked to amino acids at various distances from the amino acid predicted to occupy the p1 site of the MHC class II epitope-binding groove (tyrosine at position 11 in the HPV sequence). Specifically, the ava linker was connected to amino acids at positions-p3, -p2, -p1, relative to the tyrosine at P1 as well as to the tyrosine (the predicted P1 amino acid of the epitope). HPV1 was the epitope-only control peptide while HPV2, HPV3, HPV4, and HPV5 were hybrids with different spacer lengths. HPV6 was an HLA-A2 restricted CTL epitope that was already tested in clinical trials. The purposes of this project were: 1) Test antigen-specific enhancement of CD4+ T helper stimulation using Ii-Key hybrids and 2) To define the most active Ii-Key/HPV16 E7 (8-22) hybrid in HLA-DR4-tg mice for clinical trials in HLA-DR4+ cervical cancer patients. After defining the most active Ii-Key/HPV16 E7 (8-22) hybrid for clinical trials, work continued in order to test these hybrids in other HLA-DR-tg mice to define which hybrid(s) is (are) active for other HLA-DR allele(s).

TABLE 2

Sequences of Constructs and Hybrids.

| Construct | Sequence |
|---|---|
| HPV1 | lheymldlqpettdl [SEQ ID NO.: 3] |
| HPV2 | LRMK-ava-lheymldlqpettdl [SEQ ID NO.: 4] |
| HPV3 | LRMK-ava- heymldlqpettdl [SEQ ID NO.: 5] |
| HPV4 | LRMK-ava- eymldlqpettdl [SEQ ID NO.: 6] |
| HPV5 | LRMK-ava- ymldlqpettdl [SEQ ID NO.: 7] |
| HPV6 | ymldlqpett [SEQ ID NO.: 8] |
| HPV7 | lheymldlqpettdl ggypydvpdya [SEQ ID NO.: 12] |
| HPV17 | LRMK-ava- eymldlqpettdl ggypydvpdya [SEQ ID NO.: 13] |
| HPV11 | rahynivtf [SEQ ID NO.: 14] |

Immunization of Mice.

HLA-DR4-IE Tg mice (3 mice per group) were immunized subcutaneously at the base of the tail with 30 nmole of HPV16 E7 MHC class II hybrid, epitope-only peptide, or CTL epitope peptides. Peptides were dissolved in saline and then emulsified with an equal volume of complete Freund's adjuvant (CFA). Mice were immunized s.c. (subcutaneous) at tail base with 28 gauge of needle without leak. Three weeks following the immunization, splenic lymphocytes were taken and ELISPOT assay was performed for IFN-γ secretion against the in vitro stimulation with HPV1 (HPV16 E7 (8-22) epitope only peptide: HPV1) and HPV6 (CTL epitope).

ELISPOT Assay

Splenic lymphocytes were used in ELISPOT assays. Bulk culture lymphocytes (0.5–1.0×10$^6$ cells/well) obtained from pooled spleens of immunized animals in each group were stimulated with 2.7 nmole of HPV16 E7 (8-22) epitope-only peptide and CTL epitope (HPV6) in 96-well immunospot 200 plates for 42 h. ELISPOT assays were performed with BD Pharmingen sets for IFN-γ (cat. no. 551849) secretion according to the manufacturer's instructions. Briefly, plates were coated overnight at 4° C. with the cytokine capture antibodies. The plates were blocked with 10% fetal bovine serum (FBS) in RPMI-1640 buffer for 2 hr at RT and washed four times with PBS containing 0.05% Tween-20 (wash buffer). Suspensions of purified CD4+ T-cells were added to the cytokine antibody pre-coated plates. After 36 hr of culture for bulk cultures, or overnight incubation for purified CD4+ T-cells, the plates were washed five times with wash buffer. Biotinylated cytokine detection antibodies (2 μg/mL) were added for 2 hr at RT. The plates were washed four times with wash buffer and avidin horseradish peroxidase-conjugated (avidin-HRP) was added at 1:100 dilution from the commercial stock for a 1 hr incubation at RT. Avidin-HRP was removed by washing four times with wash buffer and two times with PBS. The spots were developed with HRP-3-amino-9-ethylcarbozole substrate (BD Pharmingen) for 30 min at RT. The plates were washed twice with sterile water and dried for 1 to 2 hr at RT.

Results:
Defining Promiscuous HLA-DR Epitopes.

Algorithm prediction indicates that HPV16 E7 (8-26) [SEQ ID NO.: 2] contains several strong overlapping HLA-DR-restricted epitopes: one beginning with tyrosine at position 11 binding to the P1-site and the other whereby methionine at position 12 occupies the P1-site. This epitope(s) is also restricted by other HLA-DR alleles. The detailed algorithm prediction scores for three potential epitopes were as follows: Epitope starting from leucine at position 8 (tyrosine at position 11 in p1) was restricted by HLA-DRB1*0401 (score=28) and by HLA-DRB*0301 (score=18). Epitope starting from histidine at position 9 (methionine at position 12 is in p1) was restricted by HLA-DRB1*0101 (score=22), by HLA-DRB1*0401 (score=20), and by HLA-DRB1*1501 (score=18). Epitope starting from glutamate at position 12 (leucine at position 15 is in p1) was restricted by HLA-DRB1*0301 (score=20), HLA-DRB1*0701 (score=22), and HLA-DRB1*1501 (score=24).

Data from HLA-DR4-tg mice.

From Table 3 (below), it can be seen that certain Ii-Key/HPV16 E7 (8-22) [SEQ ID NO.: 3] hybrids gave higher specific in vivo stimulatory activity for CD4+ activation (HLA-DR4-tg mice do not have other MHC class II alleles and HLA-A2 allele and HPV6 was not restricted by other MHC class I alleles). Among those, HPV4 gave more than five-fold enhancement of immune response than HPV1 (epitope-only peptide) which was a highly active in HLA-DR4-tg mice (Table 3), confirmed the prediction by algorithm. HPV5 gave less stimulation activity, indicating that glutamate at position 10 may be a necessary amino acid of the epitope HPV16 E7 (8-22) for in vivo stimulation in HLA-DR4 transgenic mice or that hybrid had optimal spacer between LRMK (SEQ ID NO: 11) and epitope. HPV2 and HPV3 also gave 2- and 3-fold enhancement of IFN-γ responses, respectively, indicating the requirement and flexibility of spacer length between Ii-Key motif and epitope. This result indicates that HPV4 was the most active candidate hybrid peptide (though HPV3 is also good) and should be effective for use in clinical trials for HLA-DR4+ patients who have cervical or other HPV16+ cancers. This group of hybrids will also be tested late in other HLA-DR allele-tg mice to define the most active Ii-Key/HPV16 E7 (8-22) for other HLA-DR alleles.

TABLE 3

ELISPOT assay of splenic cells from HLA-DR4-tg mice (3 mice per group) immunized with HPV hybrids in CFA.

| Constructs for in vivo immunization | IFN-γ spots/10⁶ cells stimulated in vitro by HPV1 and HPV6 | | |
|---|---|---|---|
| | medium | HPV1 | HPV6 |
| Control | 22 | 20 | 18 |
| HPV1 | 58 | 142 | 140 |
| HPV2 | 62 | 212 | 62 |

TABLE 3-continued

ELISPOT assay of splenic cells from HLA-DR4-tg mice (3 mice per group) immunized with HPV hybrids in CFA.

| Constructs for in vivo immunization | IFN-γ spots/10⁶ cells stimulated in vitro by HPV1 and HPV6 | | |
|---|---|---|---|
| | medium | HPV1 | HPV6 |
| HPV3 | 52 | 224 | 50 |
| HPV4 | 76 | 422 | 148 |
| HPV5 | 26 | 82 | 26 |
| HPV6 | 44 | 28 | 44 |

FIG. 1 shows data from a similar corroborating study wherein the most active HPV hybrids in HLA-DR4-tg mice are demonstrated. The data shows INF-gamma production from splenocytes from mice immunized with epitope only (HPV1) or Ii-key hybrids (HPV2-HPV 6) after in vitro stimulation with HPV1 or HPV4. Mice immunized with HPV4 had approximately 5-fold greater INF-gamma secreting cells than mice immunized with epitope alone (HPV1).

Linkage of the Ii-Key Motif to HLA-DR4 Epitope Increased the Binding of that Epitope to HLA-DR4 Molecules.

Figure 2:
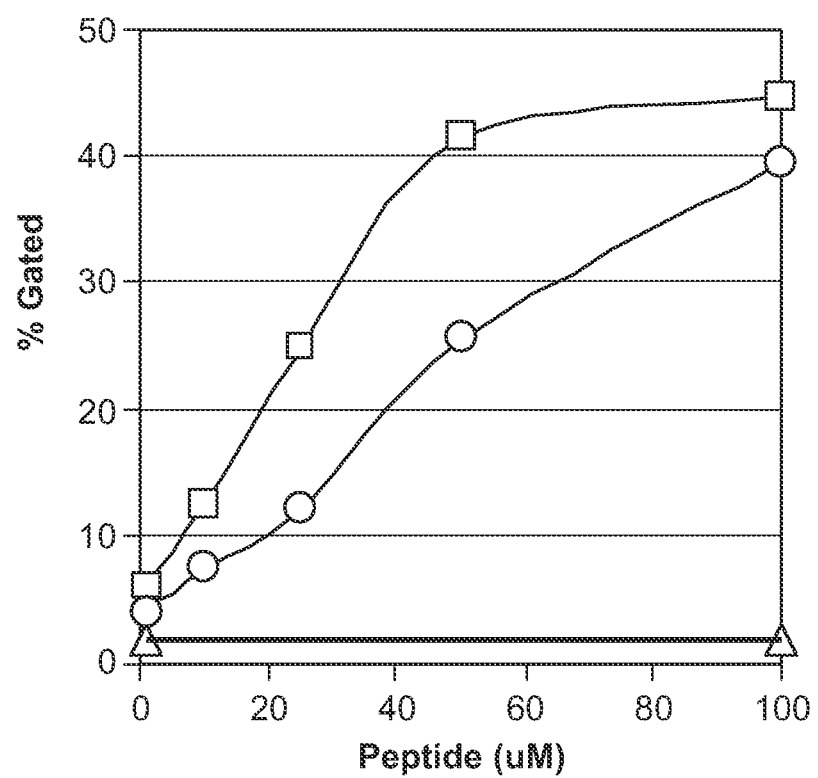
FIG. 2 shows comparison of binding of Ii-Key/HPV16 E7 epitope hybrid versus HPV16 E7 epitope-only peptide. One million HLA-DR4+H9 cells were incubated with the indicated concentrations of the HPV1-HA tagged peptide HPV7 (○) or the HPV4-HA tagged peptide HPV17 (□). After analysis by flowcytometry, the percentage of gated cells was plotted against the peptide concentration. The gate was set such that about 98% cells untreated with peptide fell out of the gate.

In order to reveal possible mechanisms for the increased potency of the HPV4 hybrid peptide, the binding affinity of HPV1 compared to HPV4 in HLA-DR4+H9 lymphoma cells was determined. Two peptides (HPV7 and HPV17) linked to an HA tag, allowing the monitoring of binding using an anti-HA monoclonal antibody, were synthesized. Specifically, HPV7 [SEQ ID NO.: 12] consisted of HPV1 extended at the C-terminus with a two-glycine residue spacer and an HA tag (YPYDVPDYA [SEQ ID NO.: 15]), while HPV 17 [SEQ ID NO.: 13] represented HPV4 similarly extended at the C-terminus with a two-glycine residue spacer and an HA tag. Different concentrations of the two peptides were first incubated with 1×10⁶ HLA-DR4+ human lymphoma cells (H9 cells) for one hour in culture medium. The binding efficiency was monitored by staining H9 cells with an anti-HA tag monoclonal antibody followed by a FITC-labeled secondary antibody. HPV17 was found to bind more efficiently than HPV7 at intermediate concentrations (10 μM to 50 μM) (Table 4 and FIG. 2). At the highest concentration (100 μM), both peptides exhibit similar binding efficiency.

TABLE 4

Binding of HPV epitope-only (HPV7) and Ii-Key/HPV hybrid (HPV17) to HLA-DR4+ Cells (H9). The numbers are percentage of positive gated cells and no peptide is 1.83%.

| | 1 nmole | 10 nmole | 25 nmole | 50 nmole | 100 nmole |
|---|---|---|---|---|---|
| HPV7 | 3.88 | 7.42 | 12.2 | 25.62 | 39.49 |
| HPV17 | 5.99 | 12.56 | 24.88 | 41.32 | 44.69 |
| No peptide | 1.83 | | | | |

Ii-Key/HPV Hybrid (HPV4) Enhanced the Potency of a Co-Immunized HPV CTL Epitope in a Dose-Dependent Manner.

Next it was shown that increased CD4+ T cell activity would induce a more robust CTL response following co-immunization of HPV4 and the H-2D$^b$-restricted CTL epitope HPV11 (HPV16 E7 (49-57) (RAHYNIVTF [SEQ ID NO.: 14]) (Feltkamp, M. C., et al., Eur. J. Immunol. 1993, 23:2242-2249). HLA-DR4-tg mice were immunized with HPV11 and varying concentrations of HPV4. The in vivo CTL assay demonstrated that the CTL epitope HPV16 E7

Figure 3:
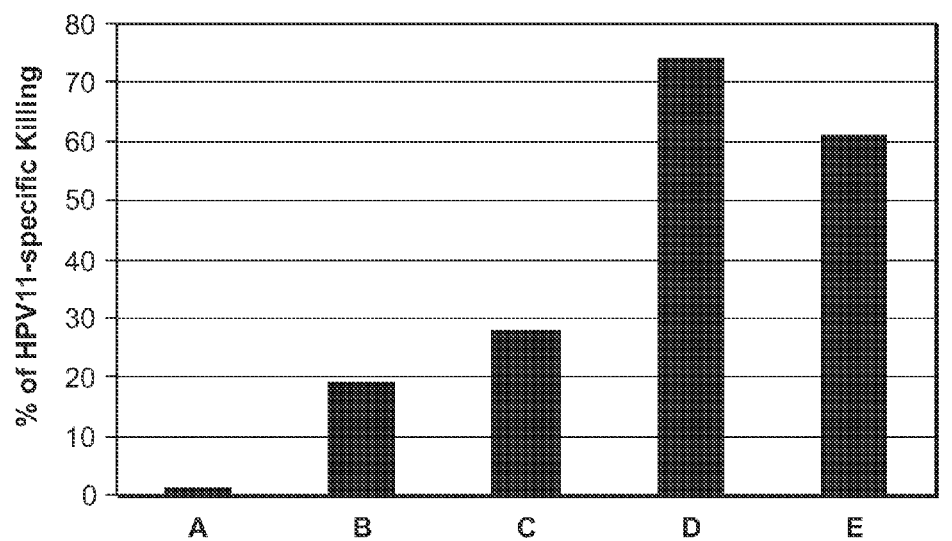
FIG. 3 shows dose dependent help by HPV4 in augmenting cytotoxic T lymphocyte (CTL) activity towards a MHC class I epitope. HLA-DR4-tg mice were immunized with no peptide (A); 60 nmole of HPV11 (HPV16 E7 (49-57) an H-2D$^b$-restricted CTL epitope) (B); 60 nmole of HPV11 plus 15 nmole HPV4 hybrid (C); 60 nmole of HPV11 plus 30 nmole HPV4 hybrid (D); or 60 nmole of HPV11 plus 60 nmole HPV4 hybrid (E). Peptides were mixed with 20 μg of CpG and then emulsified in an equal volume of IFA in a total volume of 150 μl/mouse. Three weeks after immunization, HPV11-specific CTL activity was measured in an in vivo assay whereby the cells were incubated with either the immunizing peptide (HPV11) and a high concentration of CFSE or no peptide and a low concentration of CFSE. Equal numbers of the two cell populations were mixed and injected by tail vein into mice. The top figure indicates the percentage of HPV11-specific CTL killing as determined by the ratio of $CFSE^{low}$ to $CFSE^{high}$ cells using the formula $1-CFSE^{low}/CFSE^{high}$ following flowcytometry. The histograms for each group are shown below. The data shown are from pooled splenocytes (2 mice per group).
Figure 3:
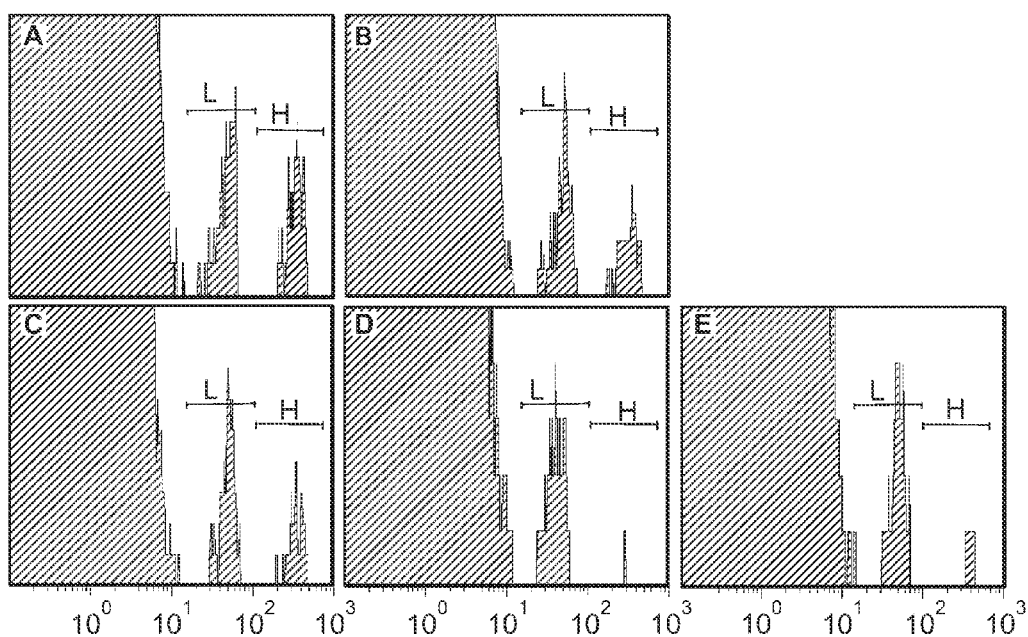

(49-57) is immunogenic in HLA-DR4-tg mice to cause epitope-specific cell killing. When co-immunized with the HPV4 hybrid, the activity of HPV16 E7 (49-57) was significantly enhanced. Maximum activity was observed in animals dosed with 30 nmole of HPV4 (Table 5 and FIG. 3). ELISPOT data revealed that the augmentation of CTL epitope activity is proportional to HPV4 activity (data not shown), demonstrating that MHC class II induced T helper activity is critical for the induction of CTL activity by peptide vaccine.

TABLE 5

Dose curve of HPV4 in helping CTL epitope: HPV11.

| Immunization | HPV11-specific CTL killing (%) |
|---|---|
| Control | 0 |
| HPV11 | 19 |
| HPV4 (15ug) + HPV11 | 28 |
| HPV4 (30ug) + HPV11 | 74 |
| HPV4 (60ug) + HPV11 | 61 |

Ii-Key Hybrid was More Potent than the Parent Epitope-Only Peptide in Augmenting the Activity of a Co-Immunized HPV CTL Epitope.

Figure 4:
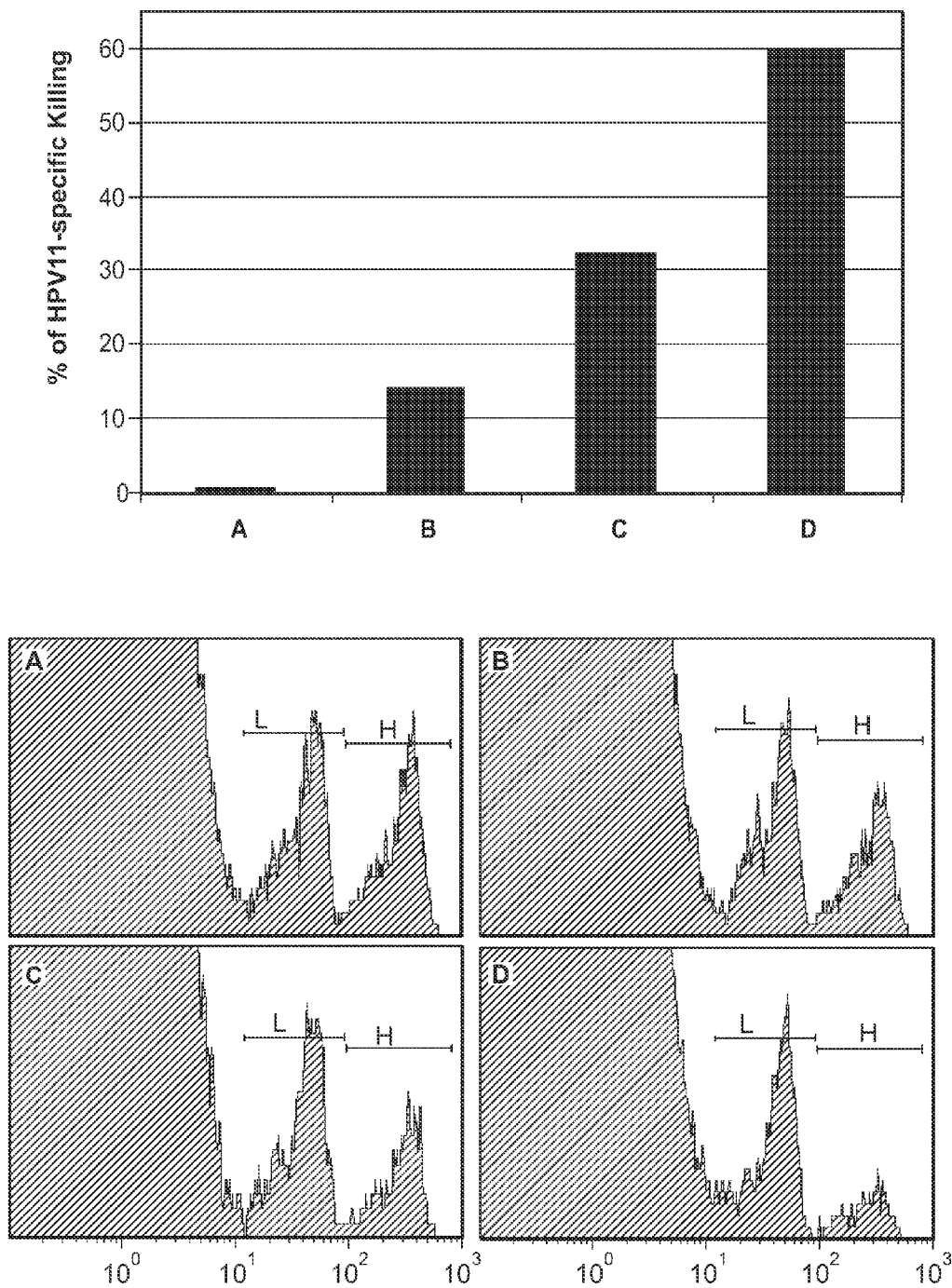
FIG. 4 shows a comparison of the activity of the Ii-Key/HPV epitope hybrid HPV4 and the epitope-only peptide HPV1 in helping specific CTL activity in vivo. HLA-DR4-tg mice were immunized with no peptide (A); 60 nmole of HPV11 (HPV16 E7 (49-57), an $H-2D^b$-restricted CTL epitope) (B); 30 nmole HPV1 plus 60 nmole HPV11 (C); or 30 nmole HPV4 plus 60 nmole HPV11. The peptides were administered as indicated for FIG. 3. Three weeks after immunization, HPV11-specific CTL activity was measured in an in vivo assay (see FIG. 3). The data shown are from pooled splenic cells (3 mice for group A and 4 mice for group B, C, and D, respectively. The top figure indicates the percentage of HPV11-specific CTL killing by determining the ratio of $CFSE^{low}$ to $CFSE^{high}$ cells using the formula $1-CFSE^{low}/CFSE^{high}$ following flowcytometry. The histograms for each group are shown below.

This experiment tested whether the Ii-Key hybrid HPV4 was more potent in enhancing the activity of the HPV CTL epitope than is the epitope-only HPV hybrid (HPV1). HLA-DR4-tg mice were immunized with either the HPV11 (HPV16 E7 (49-57)) CTL epitope peptide alone, the HPV11 CTL epitope with 30 nM HPV1, or the HPV11 CTL epitope with 30 nM HPV4. In vivo CTL analysis showed that HPV4 was more potent compared to HPV1 in enhancing the activity of the co-immunized CTL epitope. Specifically, the level of HPV11-specific cell killing was doubled in mice co-immunized with HPV4 and HPV11 compared to those co-immunized with HPV1 and HPV11 (Table 6 and FIG. 4).

TABLE 6

Comparison of augment potency of HPV1 and HPV4 in augmenting the activity of CTL epitope: HPV11.

| Co-immunization | HPV11-specific CTL activity (%) |
|---|---|
| CpG only | 0 |
| HPV11 | 14 |
| HPV1 + HPV11 | 32.5 |
| HPV4 + HPV11 | 60 |

What is claimed is:

1. A method of stimulating an immune reaction, said method comprising administering to a subject or causing to be administered to a subject a composition comprising an Ii-key/HPV16 E7 hybrid peptide or nucleic acid encoding an Ii-key/HPV16E7 hybrid peptide, wherein said Ii-key HPV 16 E7 hybrid peptide is selected from the group consisting of HPV2 represented by SEQ ID NO: 4, HPV3 represented by SEQ ID NO: 5 and HPV4 represented by SEQ ID NO: 6.

2. The method of claim 1, wherein said hybrid peptide is HPV4 represented by SEQ ID NO: 6.

3. The method of claim 1, wherein said composition further comprises a pharmaceutically accepted carrier.

4. The method of claim 1, wherein said composition comprises a nucleic acid encoding the Ii-Key/HPV 16 E7 hybrid peptide said hybrid peptide selected from the group consisting of HPV2 represented by SEQ ID NO: 4, HPV3 represented by SEQ ID NO: 5 and HPV4 represented by SEQ ID NO: 6.

* * * * *